United States Patent
Kashimoto et al.

(10) Patent No.: US 6,448,031 B1
(45) Date of Patent: Sep. 10, 2002

(54) PROCESS FOR PRODUCING LH-RH DERIVATIVES

(75) Inventors: Kazuhisa Kashimoto; Yumiko Nagano; Akiko Ohata, all of Ibaraki (JP)

(73) Assignee: Itoham Foods Inc., Kobe (JP)

( * ) Notice: Subject to any disclaimer, the term of this patent is extended or adjusted under 35 U.S.C. 154(b) by 0 days.

(21) Appl. No.: 09/463,947

(22) PCT Filed: Aug. 4, 1997

(86) PCT No.: PCT/JP97/02705

§ 371 (c)(1),
(2), (4) Date: Feb. 4, 2000

(87) PCT Pub. No.: WO99/07874

PCT Pub. Date: Feb. 18, 1999

(51) Int. Cl.$^7$ ............................. C12P 21/06; C12N 9/76
(52) U.S. Cl. ...................................... 435/68.1; 435/213
(58) Field of Search ................................ 435/68.1, 213

(56) References Cited

U.S. PATENT DOCUMENTS

| | | | |
|---|---|---|---|
| 4,100,274 A | | 7/1978 | Dutta et al. |
| 4,234,571 A | | 11/1980 | Nestor et al. |
| 5,002,872 A | * | 3/1991 | Gross |

FOREIGN PATENT DOCUMENTS

| | | | |
|---|---|---|---|
| JP | 61-13480 | | 4/1986 |

OTHER PUBLICATIONS

Kise et al., "Enantiospecificity of Alpha–Chymotrypsin at S1' Site for Peptide–Synthesis in Aqueous–Organic Media" (1993) Bull. Chem. Soc. Japan, vol. 66, No. 12, pp. 3693–3698.*

Kashimoto et al., "Enzyme Peptide Synthesis: Transesterification Catalyzed by Chymotrypsin" (1996) Pepuchido Kagaku Toronkai Koen Yoshishu, vol. 34, pp. 69, in JIC-ST–EPlus, AN 970321312.*

"Burdick & Jackson High Purity Solvent Guide, Second Edition", Burdick & Jackson Laboratories, Inc. (1982) pp. 18–21.*

Fink, A.L., "Cryoenzymology: The Use of Sub–Zero Temperatures and Fluid Solutions in the Study of Enzyme Mechanisms" (1976) J. Theor. Biol., 61, 419–445.*

Nilsson et al., "Peptide Synthesis in Aqueous–Organic Solvent Mixtures with alpha–Chymotrypsin Immobilized to Tresyl Choride–Activated Agarose" (1984) Biotech. Bioeng., 26(10), 1146–1154.*

W. Halwachs, et al., Biotechnology and Bioengineering, vol. 19, pp. 1667–1677, "Application of Immobilized Chymotryspin in a Multistage Fluidized–Bed Reactor," 1997.

W. Halwachs, et al., Biotechnology and Bioengineering, vol. 20, pp. 541–554, "Immobilized α–Chymotrypsin: Pore Diffusion Control Owing pH Gradients in the Catalyst Particles," 1978.

D. Gabel, Febs Letters, vol. 49, No. 2, pp. 280–281, "Active Site Titration of Immobilized Chymotrypsin With a Fluorogenic Reagent," Dec. 1974.

A. Kato, et al., Journal of Food Science, vol. 54, No. 5, pp. 1345–1347, "Deamidation and Functional Properties of Food Proteins by the Treatment With Immobilized Chymotrypsin at Alkaline pH," 1989.

M. Schuster, et al., Tetrahedron Letters, vol. 33, No. 20, pp. 2779–2802, α–Chymotrypsin–Catalyzed (3+7) Segment Synthesis of the Luteinzing Hormone Releasing Hormone, 1992.

N. Sherwood, et al., Proc. Natl. Acad. Sci., vol. 80, pp. 2794–2798, "Characterization of a Teleost Gonadotropin–Releasing Hormone," May 1983.

D.A. Lovejoy, et al., Regulartory Peptides, vol. 33, pp. 105–116, "Primary Structure of Two Forms of Gonadtropin–Releasing Hormone From Brains of the American Alligator (Alligator Mississippiensis)," 1991.

* cited by examiner

*Primary Examiner*—Jon P. Weber
(74) *Attorney, Agent, or Firm*—Oblon, Spivak, McClelland, Maier & Neustadt, P.C.

(57) ABSTRACT

This invention relates to a method for producing an LH-RH derivative, characterized in that a peptide fragment shown by general formula (1): pGlu-His-Trp-OR$^1$ (where R$^1$ denotes a lower alkyl) and a peptide fragment shown by general formula (2): H-Ser-Tyr-X-Leu-Arg-Pro-Y (where X denotes an amino acid selected from the group consisting of D-amino acids such as D-Leu, D-Ser(But), D-Trp, and (2-napthyl)-D-Ala, and Gly, and Y denotes Gly-NH$_2$, Azgly (Azaglycine)-NH$_2$ or NHR$^2$ (R$^2$ is lower alkyl)) are allowed to react in the presence of chymotrypsin or a chymotrypsin-like enzymes, to produce the LH-RH derivative shown by general formula (3): pGlu-His-Trp-Ser-Tyr-X-Leu-Arg-Pro-Y (where X and Y are as defined above). Since the method does not accompany a side reaction such as racemization, it enables simple separation and purification of LH-RH derivatives. Moreover the method enables to provide high yields, as well as recovery and recycling of unreacted peptide fragments, therefore it is valuable in industrial use.

13 Claims, No Drawings

PROCESS FOR PRODUCING LH-RH DERIVATIVES

This application is a 371 of PCT/JP97/02705 filed Aug. 4, 1997.

TECHNICAL FIELD

The present invention relates to an enzymatic method for effectively producing an LH-RH derivative, a useful peptide as a drug.

BACKGROUND ART

Luteinizing hormone (LH) and follicle-stimulating hormone (FSH) are released from the anterior pituitary under the control of LH-RH (luteinizing hormone releasing hormone) that is produced at the hypothalamus. LH-RH and derivatives thereof have a secretory activity of gonadotropin and are shown that the sequential administration of LH-RH and its derivatives inhibits gonad functions so that they are applied as drugs to prevent and/or treat diseases such as endometriosis, central precocious puberty, infertility, and prostate cancer. LH-RH and its derivatives that have been applied as drugs include buserelin (JP-B-60-9519 official gazette), goserelin (JP-B-61-13480), leuprorelin (JP-B-53-14072), and napharelin (JP-B-63-56238).

As a method for producing the above described LH-RH and derivatives, a chemical synthesis method by the liquid phase synthesis method wherein peptide fragments with partial sequences corresponding to the polypeptides are formed by the liquid phase or the solid phase method, then each fragment is coupled in liquid phase is known (JP-B-56-47175, JP-A-49-117468, JP-B-57-29462, JP-B-57-25540, JP-B-63-17839, JP-B-63-45398, JP-A-48-40770, JP-A-50-88069, JP-A-49-41375, JP-A-49-41376, JP-A-48-99170, JP-B-52-20996, JP-A-49-35381, JP-B-52-8831, JP-B-57-61268, JP-B-53-14072, JP-B-57-26506, JP-B-60-22720, JP-B-61-13480, and JP-B-3-71439).

However, in the liquid phase synthesis method the solubility changes subtly as the number of amino acid residues of a peptide increases, making it difficult to find an appropriate solvent. As such difficulty increases it also becomes more difficult to separate the peptide of interest from unreacted substances and from side-products. Particularly the serine residue at position 4 of LH-RH and its derivatives tends to be racemized thus remains as impurities and so recovery of raw materials is impossible. Therefore the method is not technically satisfactory since posttreatment of the reaction is difficult and uneconomical.

SUMMARY OF THE INVENTION

The object of the invention is to provide a method for efficiently producing LH-RH derivatives in a large scale at lower costs.

As a result of our intensive researches to solve the abovementioned problems, we have achieved the present invention by finding a method for producing LH-RH derivatives suitable for industrial production by means of an enzymatic synthesis.

The present invention is characterized in that a peptide fragment shown by general formula (1):

pGlu-His-Trp-OR$^1$     (1)

(where R$^1$ denotes lower alkyl) and a peptide fragment shown by general formula (2):

H-Ser-Tyr-X-Leu-Arg-Pro-Y (SEQ ID NO:4)     (2)

(where X denotes an amino acid selected from the group consisting of D-Leu, D-Ser(But), D-Trp, (2-naphthyl)-D-Ala, and Gly; Y denotes Gly-NH$_2$, Azgly (Azaglycine)-NH$_2$ or NHR$^2$ (where R$^2$ is lower alkyl)) are allowed to react in the presence of an enzyme selected from the group consisting of chymotrypsin or chymotrypsin-like enzymes to produce a LH-RH derivative shown by general formula (3):

pGlu-His-Trp-Ser-Tyr-X-Leu-Arg-Pro-Y (SEQ ID NO:1)     (3)

(where X and Y denote the same as in the above formula).

Here the present invention is characterized in that the abovementioned R$^1$ is an alkyl group having 1 to 3 carbons and R$^2$ is an alkyl group having 1 to 3 carbons. Further the present invention is characterized in that the enzyme selected from the group consisting of the chymotrypsin or chymotrypsin-like enzymes is chymotrypsin.

Moreover, the present invention is characterized in that a peptide fragment shown by general formula (4):

pGlu-His-Trp-OR$^1$     (4)

(where R$^1$ denotes lower alkyl) and a peptide fragment shown by general formula (5):

H-Ser-Tyr-X-Leu-Arg-Pro-Y (SEQ ID NO:4)     (5)

(where X denotes an amino acid selected from the group consisting of D-Leu, D-Ser(But), D-Trp, (2-naphthyl)-D-Ala, and Gly; Y denotes Gly-NH$_2$, Azgly-NH$_2$ or NHR$^2$ (where R$^2$ is lower alkyl)) are allowed to react in the presence of an enzyme selected from the group consisting of chymotrypsin or chymotrypsin-like enzymes and in a solvent in which water or buffer is mixed with organic solvent to produce LH-RH derivatives shown by general formula (6):

pGlu-His-Trp-Ser-Tyr-X-Leu-Arg-Pro-Y (SEQ ID NO:1)     (6)

(where X and Y denote the same as in the above formula).

Here the present invention is characterized in that the solvent wherein water or buffer and an organic solvent are mixed is a mixture in which water or buffer and an organic solvent miscible with water are mixed, or is a mixture in which water or buffer are saturated with an organic solvent partially miscible with water.

Moreover, the present invention is characterized in that a peptide fragment shown by general formula (7):

pGlu-His-Trp-OR$^1$     (7)

(where R$^1$ denotes lower alkyl) and a peptide fragment shown by general formula (8):

H-Ser-Tyr-X-Leu-Arg-Pro-Y (SEQ ID NO:4)     (8)

(where X denotes an amino acid selected from a group consisting of D-Leu, D-Ser(But), D-Trp, (2-naphthyl)-D-Ala, and Gly; Y denotes Gly-NH$_2$, Azgly-NH$_2$ or NHR$^2$ (where R$^2$ is lower alkyl)) are allowed to react in the presence of an immobilized enzyme that is selected from the group consisting of chymotrypsin or chymotrypsin-like enzymes and in a solvent in which water or buffer is mixed with an organic solvent to produce LH-RH derivatives shown by general formula (9):

pGlu-His-Trp-Ser-Tyr-X-Leu-Arg-Pro-Y (SEQ ID NO:9)     (9)

(where X and Y denote the same as described above).

In this specification, the LH-RH derivative is referred to as the one wherein Glycine at position 6 or at position 10 of the LH-RH shown by general formula (10) (SEQ. ID.NO:1):

PGlu-His-Trp-Ser-Tyr-Gly-Leu-Arg-Pro-Gly-NH$_2$ (10)

is substituted by a different amino acid, a special amino acid or a modified amino acid. An amino acid at the position corresponding to Gly at position 6 (hereinafter referred to as X) may be a general D-amino acid or a modified D-amino acid. For example, the D-amino acid mentioned here may be D-Leu, D-rrp, D-Ala, D-Phe, D-Val, or D-His and the modified amino acid may be D-Ser(But) or (2-naphthyl)-D-Ala. In addition, X may be an L-amino acid. When X is a D-amino acid, it is preferably selected from the group consisting of D-Leu, D-Trp, D-Ala, D-Ser(But) and (2-naphthyl)-D-Ala and when X is an L-amino acid it is preferably Glycine. Glycine at position 10 (hereinafter referred to as Y) is preferably Gly-NH$_2$, Azgly-NH$_2$ or NHR$^2$ (where R$^2$ is lower alkyl).

"Lower alkyl" used herein means an alkyl having 1 to 3 carbons such as methyl, ethyl, propyl, or isopropyl. R$^1$ is preferably a methyl or an ethyl group and R$^2$ is preferably an ethyl or a methyl group.

Besides in this specification, abbreviations used for amino acids, peptides, protecting groups, solvents and others are according to rules of International Union of Pure and Applied Chemistry (IUPAC) and of International Union of Biochemistry (IUB) or to conventional symbols in the field the present invention pertains to. Examples are shown below. Possible optical isomers of amino acids indicate L-configuration unless otherwise indicated.

Tyar: Tyrosin residue
Gly: Glycine residue
Azgly: Azaglycine residue
Glu: Glutamic acid residue
pGlu: Pyroglutamic acid residue
Ser: Serine residue
Arg: Arginine residue
Pro: Proline residue
Leu: Leucine residue
His: Histidine residue
Ala: Alanine residue
Trp: Tryptophane residue
Et: Ethyl
Boc: t-Butoxycarbonyl
Aoc: t-Amyloxycarbonyl
Bz: Benzyl
Z: Benzyloxycarbonyl
Tos: Tosyl
OMe: Methyl ester
OBz: Benzyl ester
OSu: N-Hydroxysuccinimide ester
TFA: Trifluoroacetic acid
THF: Tetrahydrofuran
DMF: Dimethylformamide
DCC: Dicyclohexylcarbodiimide
WSC: N-ethyl-N'-dimethylaminopropyl-carbodiimide
HOSu: N-hydroxysucciniimide
HOBt: 1-Hydroxybenzotriazol
MeOH: Methanol
EtOH: Ethanol
AcOH: Acetic acid The peptide fragment shown by the general formula (1) corresponds to amino acid residues at positions 1 to 3 of the amino acid sequence of the LH-RH derivative shown by the general formula (3). Further, the peptide fragment shown by the general formula (2) corresponds to amino acid residues at positions 4 to 10 of the amino acid sequence of the LH-RH derivative shown by the general formula (3).

Each of the peptide fragments shown by the general formula (1) or shown by the general formula (2) can be synthesized according to a well-known method for synthesizing peptides. For example, according to the methods described in *The Peptides*. Vol 1, Schreder and Luhke., 1966., Academic Press, New York, U.S.A., or in *Peptide Synthesis*, Izumiya et.al., 1975, Maruzen Corporation, peptide fragments can be synthesized by the azido method, acid chloride method, acid anhydride method, mixed acid anhydride method, DCC method, activated ester methods (e.g., p-nitrophenyl ester method, N-hydroxysuccinimide ester method, and cyanomethyl ester method), method using Woodword's Reagent K, carboimidazole method, oxidation-reduction method, DCC-additive (HONB, HOBt, HOSu) method, and solid phase method. With these general methods for synthesizing peptides, peptides can be produced for example by a so-called stepwise elongation method wherein one amino acid is in order condensed with a C-terminal amino acid according to the amino acid sequence or by the fragment condensation method wherein fragments each composed of several fragments are synthesized and coupled to each other.

In the reaction process for synthesizing the peptide fragments shown by the above general formula (1) or (2), functional groups that are not involved in the reaction are protected by normal protective groups, being eliminated after the completion of the reaction. Furthermore, functional groups involved in the reaction are normally activated. Each of these reaction methods is well known and the reagents used therein can be properly selected from well-known reagents.

The protective groups of amino groups include, for example, benzyloxycarbonyl (Z), t-butyloxycarbonyl (Boc), t-amyloxycarbonyl (Aoc), isobonyloxycarbonyl, p-methoxybenzyloxycarbonyl, 2-chloro-benzyloxycarbonyl, adamantyloxycarbonyl, trifluoroacetyl, phthaloyl, formyl, o-nitrophenylsulphenyl, and diphenylphosphinothioyl. Normally Boc is used to protect amino groups. But when D-Ser (But) is coupled, the use of Z group allows to remove only Z group without removing But (t-butyl) group.

The protective groups of carboxyl groups include, for example, alkylesters (for example, methyl ester, ethyl ester, propyl ester, butyl ester, and tert-butyl ester), benzyl ester, p-nitrobenzyl ester, methyl benzyl ester, p-chlorobenzyl ester, benzhydryl ester, benzyloxycarbonyl hydrazide, tert-butyloxycarbonylhydrazide, and tritylhydrazide. To hydrazidize, methyl ester or ethyl ester is preferably used.

Activated carboxyl groups involved in peptide synthesis include, for example, acid chloride, acid anhydride, mixed acid anhydride, azide, activated esters (for example, esters of pentachlorophenol, p-nitrophenol, N-hydroxysucciniimide, N-hydroxybenztriazole, and N-hydroxy-5-norbornene-2,3-dicarboxyimide). Among them the azide method with less racemization tendency is preferably used upon condensation of fragments.

In addition, peptide bond synthesis reaction may be performed in the presence of condensing agents, such as carbodiimide reagents including dicyclohexyl carbodiimide, and carbodiimidazole or in the presence of tetraethylpyrophosphate.

Usually proteolytic enzymes have been mainly used to cleave peptide bonds. Further it has been well known from old times that proteolytic enzymes can also be involved in the reverse reaction to synthesize peptide bonds. Synthesis of long-chain peptides with enzymes is limited to a case that the structure contains amino acids having a limited substrate specificity or in a case that an enzyme has a limited substrate specificity. Thus general enzymes, such as trypsin and chymotrypsin, are rarely used in peptide synthesis reactions. Accordingly, enzyme reaction is mainly used for relatively short-chain peptide bonds, such as oligopeptides, but it still takes time for examining synthesis conditions. Because of this, chemical synthesis is generally used to produce peptides, and enzymatic synthesis is tried only when in chemical synthesis many side reactions occur or reactions are difficult. Enzymatic synthesis can be extremely useful, when the synthesis is performed under mild conditions that enables mass production and the above-mentioned problems in chemical synthesis are solved with appropriate conditions.

As a result of intensive researches, the present inventors have succeeded in effectively producing LH-RH derivatives shown by the general formula (3) by allowing the peptide fragment shown by the general formula (1) and the one shown by the general formula (2) to react in the presence of chymotrypsin or a chymotrypsin-like enzyme so as to couple to each other.

Chymotrypsin utilized in the present invention is a kind of serine protease that is registered as enzyme number EC.3.4.21.1 of International Union of Biochemistry (IUB), Enzyme Committee, and is obtained from bovine pancreas. Chymotrypsin is on market and sold by SIGMA Corporation, etc.

Chymotrypsin-like enzymes are proteolytic enzymes that recognize aromatic amino acids such as Tyr and Phe, and for example include α-chymotrypsin.

Chymotrypsin or chymotrypsin-like enzymes are used preferably because one of the recognition sites of chymotrypsin or chymotrypsin-like enzymes, Trp, is present in LH-RH derivatives.

Reaction of chymotrypsin or chymotrypsin-like enzymes are performed normally in a medium containing a buffer with a pH of about 5 to about 10, preferably pH of about 6 to about 9, more preferably pH of about 7.5 to about 8.5.

The term "medium containing a buffer" used herein refers to a solvent having a buffer itself as a medium, a mixture of a buffer (selected from the various ones explained next) and an organic solvent miscible with water, or a mixture of such a buffer and an organic solvent partially miscible with water.

The buffer is not particularly limited and various buffers can be used as far as the pH is within the above range. For example, the buffer includes Tris-hydrochloric acid, MacIlvaine's buffer, phosphate buffer, ammonium acetate buffer, Atkins & Pantin buffer and Veronal buffer.

When the buffer is used as a reaction medium, the buffer is usually used by mixing with an organic solvent miscible with water. The organic solvents miscible with water include dimethylformamide (DMF), dimethylsulfoxide (DMSO), dimethylimidazolidinone (DMI), hexamethylphosphoryltriamide (HMPA), methanol (MeOH), ethanol (EtOH). Dimethylformamide, methanol, and ethanol are preferable.

In addition, an organic solvent partially miscible with water such as n-butanol (1-BuOH) or ethyl acetate (EtOAc) can be used. In the use of such an organic solvent, BuOH is preferably used to facilitate the operation of a partition chromatography in the posttreatment.

These organic solvents can be used alone or in combination of the two or more of them.

When the reaction of chymotrypsin and chymotrypsin-like enzymes is performed in a mixture of water or buffer and organic solvent, not in a solvent consisted only of water or buffer, the yield of a peptide of interest can significantly be improved.

Generally, the mixing ratio of the organic solvent miscible with water to water or buffer is preferably 50 volume % or less in view of the reactivity. When an immobilized enzyme, such as chymotrypsin immobilized with celite, is used, the preferable mixing ratio is 80 volume % or more. When an organic solvent partially miscible with water is used, there is an advantage that the use of the organic solvent saturated with water results in high reaction efficiency of enzymes.

The above described reaction of enzymes is performed within a temperature range wherein chymotrypsin or chymotrypsin-like enzymes can act, normally about 0° C. to about 50° C., preferably about 0° C. to about 20° C. The reaction at about 10° C. has an effect capable of inhibiting a hydrolysis reaction that occurs simultaneously.

Amount of chymotrypsin or of chymotrypsin-like enzymes to be used is not specifically limited and can be varied depending on reaction conditions. For example, the use of about 50 mg to about 100 mg of chymotrypsin based on 50 g of a substrate leads to the synthesis of a target peptide in a yield ranging from about 75 to about 85% after 1-hour reaction.

Normally 1 to 5 moles, or preferably 2 to 4 moles, of the peptide fragment shown by general formula (1) is used per mole of the peptide fragment shown by general formula (2).

In the method of the present invention, chymotrypsin or chymotrypsin-like enzymes dissolved in water or an appropriate buffer can be used, or those immobilized by general methods including the carrier-coupling method, crosslinking method, entrapping method, and other methods can be used as immobilized enzymes. The carriers used in the carrier-coupling method include polysaccharide derivatives, such as cellulose, dextrun, and agarose; polyacrylamide gel; celite; and porous glass. The reagents for crosslinking in the crosslinking method, for example, include glutaraldehyde, bisdiazobenzidine, N,N-polymethylenebisiodoacetamide, and N,N-ethylene bismaleinimide. The materials used in the entrapping method include, for example, polyacrylamide gel, polyacrylalcohol gel, starch, konnyaku powder, nylon, polyurea, polystyrene, ethyl cellulose, colodion, and cellulose nitrate. However, the immobilization method is not limited to those using the above methods.

In the production method according to the present invention, LH-RH derivatives shown by the following formula (11) can be obtained for example in the manner described below:

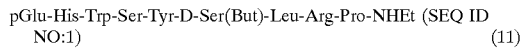

pGlu-His-Trp-Ser-Tyr-D-Ser(But)-Leu-Arg-Pro-NHEt (SEQ ID NO:1)        (11)

That is, a given amount of a peptide fragment shown by the following formula (12)

pGlu-His-Trp-OMe        (12)

and a given amount of a peptide fragment shown by the following formula (13)

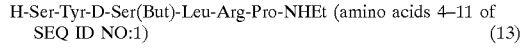

H-Ser-Tyr-D-Ser(But)-Leu-Arg-Pro-NHEt (amino acids 4–11 of SEQ ID NO:1)        (13)

are stirred in n-butanol saturated water at a pH of around 7.8 at about 10° C. for 1 hour in the presence of chymotrypsin having a given activity, to obtain the LH-RH derivative. Preferable activity of chymotrypsin is about 1000 or more international unit (U)/mg in order to facilitate the removal thereof in the posttreatment. A high yield can be obtained in the reaction using the molar ratio 3:1 of the peptide fragment shown by formula (12) to the one shown by (13). In addition, as an alternative for the addition of enzymes dissolved in water or buffer to the reaction fluid, for example, chymotrypsin immobilized with agarose according to conventional methods can be used as an immobilized enzyme. The use of immobilized enzymes facilitates removal of them by filtering the reaction fluid through a filter such as a glass filter after the completion of the reaction and allows a reuse of them.

The LH-RH derivatives can be obtained as described above and the obtained LH-RH derivatives can be purified as follows.

The LH-RH derivatives produced by the method according to the present invention can be desalted and purified by general methods. Desalting can be performed by various methods, which utilize difference in molecular sizes between the derivatives and the salt, including gel filtration, ultrafiltration, and dialysis. For example, it can be performed by ultrafiltration using a membrane made of cellulose acetate, gel filtration using Sephadex column such as Sephadex LH-20, Sephadex-60, Sephadex G-25, and ion-exchange chromatography using e.g., DEAE-cellulose. In purification, liquid chromatography including partition chromatography wherein two types of liquids that are not miscible with each other (e.g., water and n-butanol) are employed and the difference in partition coefficients between the two liquid phases is utilized, normal phase chromatography using a solid phase such as silica gel, and reversed phase chromatography using a solid phase such as ODS-silica gel can be used by such as high performance liquid chromatography (HPLC).

For example, since the LH-RH derivative produced by the methods according to the present invention is hydrophilic, the derivatives can be purified by using organic solvent that is not completely miscible with water as shown below. The mixture reacted as described above is extracted by using the organic solvent, partitioned by adding water to the extracted fluid, then solidified with a solvent such as ether. A preferable organic solvent for the extraction is n-butanol (n-BuOH). Such a solvent can lead high extractability because of its high polarity and it is not miscible with water, so that it is convenient for the subsequent partition chromatography process.

Three hundred ml of n-butanol (about ¼ of the volume of the reaction mixture) is added to the reaction mixture (1200 ml) to perform partition chromatography between the n-butanol and the water in the reaction mixture. Extraction with n-butanol can be repeated if necessary. The aqueous layer and the organic layer are concentrated separately. The above peptide fragment (7) recovered from the aqueous layer can be reused for the later reaction.

It is preferable that the roughly purified product obtained from the organic layer by partition chromatography solidifies by using a solvent such as diethyl ether or ethyl acetate, because LH-RH derivatives are slightly soluble in such a solvent. Then the solidified product is dissolved in an appropriate buffer like ammonium acetate, and fractioned by column chromatography with a proper solid phase and a mobile phase. The use of a weak cation exchange resin such as CM cellulose or a strong cation resin such as SP allows to obtain interaction with the Arg residues contained in LH-RH. The use of a buffer (which is the same buffer used when the solidified roughly purified product is dissolved) as a mobile phase has an advantage of resulting in a high yield when the salt concentration is increased in a linear gradient. For example, 0.01M aqueous ammonium acetate solution and 0.1M aqueous ammonium acetate solution can be used. The resulting eluate can be purified with HPLC properly selecting a solid phase and an eluent. In HPLC, ODS silica column, e.g. TSK gel ODS-120T, can be used as a solid phase and the use of ODS silica column is the most suitable. Furthermore, 0.1% TFA-acetonitrile can be used as a mobile phase. Here, the content of acetonitrile is increased by 1% per minute from the beginning 0.1% TFA-20% acetonitrile so as to obtain a linear gradient of 0.1%TFA-50%acetonitrile, then the target LH-RH derivative can be separated well. Purification is not limited to the abovementioned methods. Moreover, when immobilized enzymes are used, ion exchange can be performed without subjecting to partition chromatography.

The method for producing LH-RH derivatives according to the present invention is more useful industrially because it has advantages as follows compared with known conventional methods.

i) Since LH-RH derivatives can be synthesized without side reactions (e.g., racemization) because of the property of an enzymatic reaction, the LH-RH derivatives can be easily purified and separated.

ii) A high yield of an LH-RH derivative can be obtained. Moreover unreacted fragments can be recovered and reused thus the method is economically advantageous.

The LH-RH derivatives may be changed to pharmaceutically acceptable salts, such as their acetate, hydrochloride and phosphate, if necessary.

EXAMPLES

More detailed description of the present invention will be given by using the following examples but the present invention is not limited thereto.

In the following examples, pure peptides obtained are identified by measuring a retaining time in the high performance liquid chromatography (HPLC), and an optical rotation, and by analyzing amino acids. Unless otherwise specified, they are measured by the following measuring methods and conditions.

(1) High Performance Liquid Chromatography (HPLC)

In HPLC analysis, LC-Module-1 (manufactured by Japan Waters Limited Corporation) is used as a detector.

(HPLC analysis conditions)

Column: TSK gel ODS-120T (4.6×250 mm)

Eluent: 0.1% TFA-acetonitrile (A linear gradient; acetnitrile is increased by 1% per minute from 20% to 50%)

Flow rate: 1 mL/min

Detection wavelength: 220 nm (2) Optical rotation

In measurement of an optical rotation, DIC-370 (manufactured by JASCO Corporation) is used.

(Measuring conditions for optical rotation)

Beam of light: Na lamp 589 nm

Temperature: 20° C.

Layer length: 100 mm

Concentration: 5 mg/ml (3) Amino Acid Composition

In amino acid composition obtained peptides are hydrolyzed in 6N hydrochloric acid (containing 0.1% phenol) at 110° C. for 20 hours then the amino acids are analyzed by using Hitachi amino acid analyzer L-8500 (manufactured by Hitachi Ltd.).

Example 1

Production of pGlu-His-Trp-Ser-Tyr-D-Ser(But)-Leu-Arg-Pro-NHEt (SEQ ID NO1)

(1-1) Production of Boc-Arg(Tos)-Pro-NHEt

First, 214.3 g of Boc-Arg(Tos)-OH was dissolved in a mixture of 150 mL of THF and 100 mL of DMF, then cooled with dry ice—ethanol to −20° C. Next, 35 mL of N-methyl morpholine, and then 66 mL of isobutyl chloroformate were added dropwise to the mixture, and stirred at −20° C. for 1 minute, thereby producing a mixed acid anhydride. The resulting reaction mixture was mixed with a solution in which 71.1 g of H-Pro-NHEt was dissolved in 300 mL of THF, and stirred at 0° C. for 5 minutes then at room temperature for 30 minutes. Subsequently, the obtained reaction mixture was concentrated under reduced pressure. Ethyl acetate 1200 mL was added twice to the residue, the residue was washed twice with 500 mL of water, then the ethyl acetate layer was concentrated under reduced pressure. The residue was solidified by treatment with ether, and the product was dried. Thus 221.18 g of Boc-Arg(Tos)-Pro-NHEt (80.0% yield) was obtained.

The melting point, optical rotation, Rf of TLC and elementary analysis of Boc-Arg(Tos)-Pro-NHEt are shown below.

m.p.: 100–102° C.; $[\alpha]_D$: −30.3 (c=1.0, MeOH); Rf: 0.69 (BuOH/AcOH/$H_2O$=4/1/5); Elementary analysis ($C_{25}H_{40}N_6O_6S.H_2O$); Calculated C, 52.61%; H, 7.42%; N, 14.73%; Found C, 52.85%; H, 7.30%; N, 14.41%.

(1-2) Production of Z-Leu-Arg(Tos)-Pro-NHEt

Boc-Arg(Tos)-Pro-NHEt 110.54 g produced as described in (1-1) was dissolved in 150 mL of dichloromethane (DCM). TFA 150 mL was added with ice cooling to the solution, then the mixture was stirred at room temperature for 30 minutes. The resulting reaction mixture was concentrated under reduced pressure. Next 1500 mL of ether was added to the residue to solidify the product, which was then dried. Thus H-Arg(Tos)-Pro-NHEt.TFA was obtained.

The deprotected H-Arg(Tos)-Pro-NHEt.TFA was dissolved in a mixture of 80 mL of DMF and 200 mL of THE, then the solution was cooled and neutralized with N-methyl morpholine. Next, 200 mL of THE, in which 53.06 g of Z-Leu-OH and 23.02 g of HOSu were dissolved, and 36.4 mL of WSC were added to the neutralized solution then the mixture was stirred at 0° C. for 5 minutes and at room temperature for overnight. After the confirmation with ninhydrin, the reaction mixture was concentrated under reduced pressure.

After 1500 mL of ethyl acetate was added to the residue, the mixture was washed twice with 500 mL of water and twice with 500 mL of saturated saline, respectively. Next the ethyl acetate layer was concentrated under reduced pressure and the residue was treated with ether to solidify the product, which was then dried. Thus 119.5 g of Z-Leu-Arg(Tos)-Pro-NHEt (85.1% yield) was obtained.

The melting point, optical rotation, Rf of TLC and elementary analysis of Z-Leu-Arg(Tos)-Pro-NHEt are shown below.

m.p.: 99–103° C.; $[\alpha]_D$: −40.6 (c=1.0, MeOH); Rf: 0.75 (BuOH/AcOH/$H_2O$=4/1/5); Elementary analysis ($C_{34}H_{49}N_7O_7S$); Calculated C, 58.35%; H, 7.06%; N, 14.01%; Found C, 58.40%; H, 7.26%; N, 13.78%.

(1-3) Production of Z-D-Ser(But)-Leu-Arg-Pro-NHEt (amino acids 3–6 of SEQ ID NO:4)

Anisole 32 mL was added to 20.99 g of Z-Leu-Arg(Tos)-Pro-NHEt produced as described in (1-2). Subsequently about 200 mL of HF was added to the solution while cooling to −70° C. with dry ice—ethanol, then the mixture was stirred at 0° C. for 1 hour. Next the product was concentrated under reduced pressure, then the residue was treated with ether. The deposited product was filtered, then vacuum drying of the product was performed on sodium hydroxide, thereby obtaining H-Leu-Arg-Pro-NHEt.HF.

Z-D-Ser(But)-OH 8.86 g was dissolved in 100 mL of THF. The solution was cooled to −20° C. with dry ice—ethanol. Then 3.3 mL of N-methylmorpholine and then 3.96 mL of isobutyl chloroformate were added dropwise to the solution, and the mixture was stirred at −20° C. for 1 minute, thereby producing a mixed acid anhydride. The resulting reaction mixture was mixed with 200 mL of a solution (neutralized with N-methylmorpholine) of H-Leu-Arg-Pro-NHEt.HF in DMF, then the mixture was stirred at 0° C. for 5 minutes then at room temperature for 30 minutes. Subsequently, the product was concentrated under reduced pressure. Water 500 mL was added to the residue then the product was extracted five times with 200 mL of n-butanol. The extract was washed five times with water. Next the n-butanol layer was concentrated under reduced pressure, the residue was then solidified by treatment with ether. Thus 22.89 g of Z-D-Ser(But)-Leu-Arg-Pro-NHEt (90.5% yield) was obtained.

The melting point, optical rotation, Rf of TLC and elementary analysis of Z-D-Ser(But)-Leu-Arg-Pro-NHEt are shown below.

m.p.: 121–123° C.; $[\alpha]_D$: −49.0 (c=1.0, MeOH); Rf: 0.51 (BuOH/AcOH/$H_2O$=4/1/5); Elementary analysis ($C_{34}H_{56}N_8O_7$); Calculated C, 59.28%; H, 8.19%; N, 16.27%; Found C, 59.01%; H, 8.15%; N, 16.19%.

(1-4) Production of Z-Ser-Tyr-OMe

Z-Ser-OH 23.9 g and 23.2 g of H-Tyr-OMe were dissolved in 50 mL of DMF, 12.7 g of HOSu and 20 mL of WSC were added to the solution, then the mixture was stirred at 0° C. for 5 minutes then at room temperature overnight. After confirmation with ninhydrin, the reaction mixture was concentrated under reduced pressure. Ethyl acetate 500 mL was added to the residue, and the mixture was washed twice with 200 mL of 1N hydrochloric acid, twice with 200 mL of saturated aqueous sodium bicarbonate, twice with saturated saline, in this order. The ethyl acetate layer was concentrated under reduced pressure. The residue was solidified by treatment with hexane. Thus 38.44 g of Z-Ser-Tyr-OMe (92.3% yield) was obtained.

The melting point, optical rotation, Rf of TLC and elementary analysis of Z-Ser-Tyr-OMe are shown below.

m.p.: 49–53° C. (decomp.); $[\alpha]_D$: +2.3 (c=1.0, MeOH); Rf: 0.89 (BuOH/AcOH/$H_2O$=4/1/5); Elementary analysis ($C_{21}H_{24}N_2O_7$); Calculated C, 60.57%; H, 5.81%; N, 6.73%; Found C, 60.88%; H, 5.88%; N, 6.99%.

(1-5) Production of Z-Ser-Tyr-$NHNH_2$

Z-Ser-Tyr-OMe 38.0 g as produced in the above (1-4) was dissolved in 200 mL of methanol. Hydrazine 50 g was added to the solution, then the mixture was allowed to stand at room temperature overnight. Next the product was concentrated under reduced pressure, and the residue was washed with methanol. Thus 34.2 g of Z-Ser-Tyr-$NHNH_2$ (90.0% yield) was obtained.

The melting point, optical rotation, Rf of TLC and elementary analysis of Z-Ser-Tyr-$NHNH_2$ are shown below.

m.p.: 194–197° C.; $[\alpha]_D$: +9.9 (c=1.0, DMF); Rf: 0.64 (BuOH/AcOH/$H_2O$=4/1/5); Elementary analysis ($C_{20}H_{24}N_4O_6$); Calculated C, 57.69%; H, 5.81%; N, 13.45%; Found C, 57.85%; H, 5.83%; N, 13.49%.

(1-6) Production of Z-Ser-Tyr-D-Ser(But)-Leu-Arg-Pro-NHEt (SEQ ID NO:4)

Z-D-Ser(But)-Leu-Arg-Pro-NHEt 28.0 g produced in the above (1–3) was dissolved in 300 mL of methanol, then hydrogen was passed to the solution in the presence of 2.5 g of 10% palladium/carbon. After stirring at room temperature for 7 hours, the catalyst was removed from the reaction mixture, the filtrate was concentrated under reduced pressure, then the residue was treated with ether. Thus H-D-Ser(But)-Leu-Arg-Pro-NHEt was obtained.

Z-Ser-Tyr-NHNH$_2$ 20.1 g produced in the above (1-5) was dissolved in 150 mL of DMF, then the solution was cooled to $-20°$ C. with dry ice—ethanol. 4N HCl-dioxane 43.5 mL and 6.5 mL of isoamyl nitrite were added to the solution to obtain an azide compound. Further, 24.4 mL of trimethylamine was added to neutralize the reaction mixture. The mixture was transferred into 150 ml of DMF solution containing H-D-Ser(But)-Leu-Arg-Pro-NHEt, stirred at $-20°$ C. for 2 hours and at $4°$ C. for 17 hours, and then concentrated. Next 500 mL of water was added to the residue, and the mixture was extracted 5 times with 200 mL of n-butanol. The extract was washed 5 times with water, the n-butanol layer was concentrated under reduced pressure, and then the residue was treated with ether to solidify the product. Thus 33.2 g of Z-Ser-Tyr-D-Ser(But)-Leu-Arg-Pro-NHEt was obtained (87.5% yield).

The melting point, optical rotation, Rf of TLC and elementary analysis of Z-Ser-Tyr-D-Ser(But)-Leu-Arg-Pro-NHEt are shown below.

m.p.: 115–118° C. (decomp.); $[\alpha]_D$: -27.6 (c=1.0, DMF); Rf: 0.36 (BuOH/AcOH/H$_2$O=4/1/5); Elementary analysis (C$_{46}$H$_{70}$N$_{10}$O$_{11}$); Calculated C, 58.83%; H, 7.51%; N, 14.91%; Found C, 58.88%; H, 7.55%; N, 14.90%.

(1-7) Production of Z-pGlu-His-OH

Z-pGlu-OH 52.6 g was dissolved in 400 mL of THF. The solution was cooled to $-20°$ C. with dry ice—ethanol. N-methylmorpholine 22.0 mL and then 26.4 mL of isobutyl chloroformate were added dropwise to the solution, then the mixture was stirred at $-20°$ C. for 1 minute, thereby producing a mixed acid anhydride. HOSu 25.3 g was added to the resulting reaction mixture then stirred for 30 minutes. Next a solution in which 62.9 g of H-His-OH.HCl and 28.0 mL of triethylamine (TEA) were dissolved in 400 mL of water was added to the mixture. After stirring at 0° C. for 1 hour and at room temperature overnight, the reaction mixture was concentrated under reduced pressure. The residual aqueous solution was washed with ethyl acetate, and the aqueous layer was extracted with n-butanol. The extract was washed with water for several times, then the n-butanol layer was concentrated under reduced pressure. After the residue was solidified with ether, it was dissolved in water and adjusted at pH 5. The solution was applied to a column (5.0×20 cm) filled with HP-20, washed with water until Pauli reaction of the effluent shows ±, and eluted from methanol. The eluted methanol fluid was concentrated under reduced pressure. The residue was treated with ether, then recrystallized from methanol-ether. Thus 59.5 g of Z-pGlu-His-OH (74.3% yield) was obtained.

The melting point, optical rotation, Rf of TLC and elementary analysis of Z-pGlu-His-OH are shown below.

m.p.: 146–149° C. (decomp.); $[\alpha]_D$: -0.91 (c=1.0, DMF); Rf: 0.14 (BuOH/AcOH/H$_2$O=4/1/5); Elementary analysis (C$_{19}$H$_{20}$N$_4$O$_6$); Calculated C, 57.00%; H, 5.03%; N, 13.99%; Found C, 57.23%; H, 5.05%; N, 14.05%.

(1-8) Production of Z-pGlu-His-Trp-OMe

Z-pGlu-His-OH 40.0 g produced in the above (1-7), H-Trp-OMe.HCl 19.6 g, and HOSu 12.7 g were dissolved in 100 mL of DMF. Next with cooling the solution was neutralized with N-methylmorpholine, 2.0 mL of WSC was added, then the mixture was stirred at 0° C. for 5 minutes and at room temperature overnight. After confirmation with ninhidryn, the reaction mixture was concentrated under reduced pressure. Ethyl acetate-n-butanol (1:1) 200 mL was added to the residue then the organic layer was washed three times with 100 mL of water. The organic layer was concentrated under reduced pressure. The residue was solidified by treatment with ether. Thus 48.5 g of Z-pGlu-His-Trp-OMe (92.3% yield) was obtained.

The melting point, optical rotation, Rf of TLC and elementary analysis of Z-pGlu-His-Trp-OMe are shown below.

m.p.: 112–115° C. (decomp.); $[\alpha]_D$: -1.5(c=1.0, DMF); Rf: 0.3 (BuOH/AcOHMH$_2$O=4/1/5); Elementary analysis (C$_{31}$H$_{32}$N$_6$O$_7$); Calculated C, 61.99%; H, 5.37%; N, 13.99% Found C, 61.54%; H, 5.33%; N, 13.80%.

(1-9) Production of pGlu-His-Trp-OMe

Z-pGlu-His-T-OMe 40.0 g produced in the above (1–8) was dissolved in 50 mL of DMF. Hydrogen was passed to the solution in the presence of 500 mg of 10% palladium/carbon. Next the mixture was stirred at room temperature for 7 hours, the catalyst was removed from the solution, then the filtrate was concentrated under reduced pressure. The residue was solidified by treatment with ether. Thus 28.5 g of pGlu-His-Trp-OMe (91.8% yield) was obtained.

The melting point, optical rotation, Rf of TLC and elementary analysis of pGlu-His-Trp-OMe are shown below.

m.p.: 132–137° C. (decomp.); $[\alpha]_D$: +4.1 (c=1.0, DMF); Rf: 0.18 (BuOH/AcOH/H$_2$O=4/1/5); Elementary analysis (C$_{23}$H$_{28}$N$_6$O$_5$); Calculated C, 59.22%; H, 5.62%; N, 18.02%; Found C, 59.01%; H, 5.55%; N, 17.89%.

(1-10) Production of H-Ser-Tyr-D-Ser(But)-Leu-Arg-Pro-NHEt (amino acids 114 6 of SEQ ID NO:1)

Z-Ser-Tyr-D-Ser(But)-Leu-Arg-Pro-NHEt 93.0 g produced as described in the above (1-6) was dissolved in 800 mL of methanol, then hydrogen was passed to the solution in the presence of 5.0 g of 10% palladium/carbon. After the mixture was stirred at room temperature for 7 hours, the catalyst was removed from the solution, then the filtrate was concentrated under reduced pressure. The residue was solidified by the treatment with ether. Thus 74.0 g of H-Ser-Tyr-D-Ser(But)-Leu-Arg-Pro-NHEt (90.3% yield) was obtained.

The melting point, optical rotation, Rf of TLC and elementary analysis of H-Ser-Tyr-D-Ser(But)-Leu-Arg-Pro-NHEt are shown below.

m.p.: 124–128° C. (decomp.); $[\alpha]_D$: +10.1 (c=1.0, DMF); Rf: 0.16 (BuOH/AcOH/H$_2$O=4/1/5); Elementary analysis (C$_{38}$H$_{64}$N$_{10}$O$_9$); Calculated C, 56.70%; H, 8.01%; N, 17.40%; Found C, 56.55%; H, 7.97%; N, 17.18%.

(1-11) Production of pGlu-His-Trp-Ser-Tyr-D-Ser(But)-Leu-Arg-Pro-NHEt (SEQ ID NO:1)

pGlu-His-Trp-OMe 30 g produced as described in (1-9) and 22 g of H-Ser-Tyr-D-Ser(But)-Leu-Arg-Pro-NHEt produced as described in (1-10) were dissolved in 1300 mL of n-butanol saturated water. The solution was adjusted at pH 7.8 with 1M hydrochloric acid or aqueous ammonia. To the solution, a solution wherein 78 mg of chymotrypsin (1000 U/mg) was dissolved in 2.5 mL of n-butanol saturated water was added, then the mixture was stirred at 10° C. for 1 hour. Then 300 mL of n-butanol was added to the reaction mixture so that the synthesized peptides were partitioned between water and n-butanol thus separated into a lower layer (aqueous layer) and an upper layer (n-butanol layer). n-Butanol 200 mL was added to the lower layer, and the same partition chromatography was repeated for three times.

The upper layer was washed 5 times with 100 mL of water, the organic and the aqueous layers were concentrated separately then solidified with ether, respectively. H-Ser-Tyr-D-Ser(But)-Leu-Arg-Pro-NHEt recovered from the aqueous layer is to be recycled for the reaction. The organic layer (n-butanol) was concentrated, and ether was added to the residue to be powdered.

The powder obtained from the organic layer was dissolved in 0.01M aqueous ammonium acetate solution, then the solution was applied to a column (4×30 cm) filled with CM-cellulose. The linear gradient elution (60 mL/hour) of 0.01M to 0.1M aqueous ammonium acetate solution (pH 4.4, 500 mL) was performed and the eluate was fractionated in volume of 10 mL each. The eluate was analyzed by high performance liquid chromatography. The target fractions were pooled and freeze-dried. Thus, 22.4 g of pGlu-His-Trp-Ser-Tyr-D-Ser(But)-Leu-Arg-Pro-NHEt (74.9% yield) was obtained.

The optical rotation, elementary analysis, and amino acid composition of pGlu-His-Trp-Ser-Tyr-D-Ser(But)-Leu-Arg-Pro-NHEt are shown below.

$[\alpha]_D$: −46.0 (c=1, $H_2O$); Elementary analysis ($C_{60}H_{86}N_{16}O_{13}\cdot CH_3COOH\cdot 2\ H_2O$); Calculated C, 55.76%; H, 7.09%; N, 16.78%; Found C, 55.60%; H, 7.10%; N, 16.79%.

Amino acid composition; Ser 2.05(2), Glu 1.08(1), Pro 0.99(1), Leu 1.09(1), Tyr 0.92(1), His 0.93(1), Arg 1.06(1).

(1-12) Synthesis of pGlu-His-Trp-Ser-Tyr-D-Ser(But)-Leu-Arg-Pro-NHEt (SEQ ID NO:1)

(1) Synthesis of pGlu-His-Trp-Ser-Tyr-D-Ser(But)-Leu-Arg-Pro-NHEt pGlu-His-Tryp-OMe 2.00 g produced as described in (1-9) and 1.30 g of H-Ser-Tyr-D-Ser(But)-Leu-Arg-Pro-NHEt produced as described in (1-10) were dissolved in 200 mL of water, then adjusted at pH 7.8 with 1M hydrochloric acid or aqueous ammonia. To the solution was suspended immobilized chymotrypsin (agarose carrier, 2000 U/g) 2.5 g. After it was confirmed that the mixture has a pH of 7.8, it was stirred at 10° C. for 1 hour. The reaction mixture was filtered through a glass filter to remove the immobilized cymotrypsin.

The filtrate was concentrated and applied to a column (4×30 cm) filled with CM-cellulose. The linear gradient elution (60 mL/hour) of 0.01M to 0.1M aqueous ammonium acetate (pH4.4, 500 mL) was performed and the eluate was fractioned in volumes of 10 mL each. The eluate was then analyzed by HPLC. The target fractions were pooled and freeze-dried. Thus 1.45 g of pGlu-His-Trp-Ser-Tyr-D-Ser (But)-Leu-Arg-Pro-NHEt (82.4% yield) was obtained.

The melting point, optical rotation, Rf value of TLC and elementary analysis of the obtained compound are identical to those of pGlu-His-Trp-Ser-Tyr-D-Ser(But)-Leu-Arg-Pro-NHEt produced as described in (1-11).

(2) Investigation of substrate specificity

Under the enzymatic reaction conditions as described above, reaction was conducted with peptides as substrates as shown in Table 1. After two hours of the reaction the synthesized peptides were analyzed by HPLC. Yields were calculated from the area of each peak.

TABLE 1

| Substrate used | Yield (%) |
| --- | --- |
| pGlu-His-Trp-OMe + H-Ser-Tyr-D-Ser(tBu)-Leu-Arg-Pro-NHEt | 78.8 |
| pGlu-His-D-Trp-OMe + H-Ser-Tyr-D-Ser(tBu)-Leu-Arg-Pro-NHEt | 0.0 |
| pGlu-D-His-Trp-OMe + H-Ser-Tyr-D-Ser(tBu)-Leu-Arg-Pro-NHEt | 7.8 |
| pGlu-His-Trp-OMe + H-D-Ser-Tyr-D-Ser(tBu)-Leu-Arg-Pro-NHEt | 0.0 |

As shown in Table 1, when the substrate wherein the Trp, a recognition site for the enzyme, has a D-configuration was used, the yield was 0% and the reaction did not proceed at all. In addition when the substrate wherein the His adjacent to N terminal side of a recognition site for the enzyme has a D-configuration was used, the yield was as low as 7.8% but the presence of the product was confirmed. When the substrate wherein the Ser, a binding site for the enzyme, has a D-configuration was used, the yield was again 0% and the reaction did not proceed at all.

Accordingly, it was shown that when enzymatic synthesis was used, racemization of Ser and His becomes difficult to occur because of the enzyme's substrate specificity, therefore products with high optical purity can be obtained.

Example 2

In this example, pGlu-His-Trp-Ser-Tyr-D-Ser(But)-Leu-Arg-Pro-NHEt was produced in the same manner as in Example 1 except that Z-D-Ser(But)-Leu-Arg-Pro-NHEt produced according to (1-1) to (1-3) of Example 1 was produced according to the following (2-1) to (2-3).

(2-1) Production of Z-Leu-Arg-$NHNH_2$

Z-Leu-OH 172.5 g and H-Arg-OEt·2HCl 178.9 g were added to 800 mL of a DMF/THF(1/1) mixed solution. The solution was neutralized by adding 143 mL of N-methylmorpholine at 0° C. Next 147.5 mL of DCC was added to the solution and then it was stirred at 0° C. for 5 minutes and at room temperature for 15 hours. The reaction solution was concentrated under reduced pressure then 1000 mL of water was added to the residue obtained. After the product was washed twice with 500 mL of ethyl acetate, the aqueous layer was extracted three times with 1000 mL of n-butanol. The obtained n-butanol layer was concentrated under reduced pressure to obtain Z-Leu-Arg-OEt.

Z-Leu-Arg-OEt was dissolved in 500 mL of methanol. $NH_2NH_2\cdot H_2O$ 150 mL was added with ice cooling to the solution, then the mixture was stirred at room temperature for 18 hours. The reaction mixture was concentrated under reduced pressure, 500 mL of water was added to the obtained residue, then the product was extracted 5 times with 1000 mL of n-butanol. The extract was washed 4 times with 500 mL of water, then concentrated under reduced pressure. The resulting residue was solidified by treatment with ether, then it was dried. Thus, 209.7 g of Z-Leu-Arg-$NHNH_2$ (74.1% yield) was obtained.

The melting point, optical rotation, Rf of TLC and elementary analysis of Z-Leu-Arg-$NHNH_2$ are shown below.

m.p.: 105–107° C.; $[\alpha]_D$: −30.6 (c=1.0, MeOH); Rf: 0.60 (BuOH/AcOH/$H_2O$=4/1/5); Elementary analysis ($C_{20}H_{33}N_7O_4$); Calculated C, 55.61%; H, 7.64%; N, 22.51%; Found C, 55.84%; H, 7.42%; N, 22.41%.

(2-2) Production of Z-Leu-Arg-Pro-NHEt

Z-Leu-Arg-$NHNH_2$ 130.8 g produced as described in the above (2-1) was dissolved in 500 mL of DMF and the solution was cooled to −20° C. with dry ice—ethanol. Then 225 mL of 4N HCl-dioxane and 40.5 mL of isoamyl nitrite were added to the solution so as to obtain an azide compound.

Further 126 mL of triethylamine was added to neutralize the mixture. The neutralized mixture was transferred to 200 mL of DMF containing 42.6 g of H-Pro-NHEt, stirred at −20° C. for 2 hours and at 4° C. for 16 hours, and concentrated. Water 800 mL was added to the residue, then the mixture was washed twice with 400 mL of ethyl acetate. The aqueous layer was extracted 3 times with 800 mL of butanol, then washed with 400 mL of water. The obtained n-butanol layer was concentrated under reduced pressure. The resulting residue was solidified by treatment with ether, and dried. Thus 154.5 g of Z-Leu-Arg-Pro-NHEt (94.3% yield) was obtained.

The melting point, optical rotation, Rf of TLC and elementary analysis of Z-Leu-Arg-Pro-NHEt are shown below.

m.p.: 125–126° C.; $[\alpha]_D$: −66.6 (c=1.0, MeOH); Rf: 0.45 (BuOH/AcOH/H$_2$O=4/1/5); Elementary analysis ($C_{27}H_{43}N_7O_5$); Calculated C, 59.43%; H, 7.94%; N, 17.97%; Found C, 59.31%; H, 7.78%; N, 18.13%.

(2-3) Production of Z-D-Ser(But)-Leu-Arg-Pro-NHEt (amino acids 3–6 of SEQ ID NO:4)

Z-Leu-Arg-Pro-NHEt 154.5 g produced as described in the above (2-2) was dissolved in 1500 mL of methanol, and hydrogen was passed to the solution in the presence of 14 g of 10% palladium/carbon. The mixture was stirred at room temperature for 16 hours, then the catalyst was removed from the mixture. The obtained filtrate was concentrated under reduced pressure to obtain H-Leu-Arg-Pro-NHEt.

Z-D-Ser(But)-OH 82.3 g was dissolved in 200 mL of THF. The solution was cooled to −20 ° C. with dry ice—ethanol. Next 30.7 mL of N-methylmorpholine and subsequently 36.3 mL of isobutyl chloroformate were added dropwise, then the reaction solution was stirred at −20° C. for 1 minute, thereby producing a mixed acid anhydride. The obtained reaction mixture was mixed with 700 mL of a DMF solution containing H-Leu-Arg-Pro-NHEt, then stirred at 0° C. for 5 minutes and at room temperature for 30 minutes.

Subsequently, the reaction mixture was concentrated under reduced pressure, and 1000 mL of water was added to the residue. The mixture was washed twice with 500 mL of ethyl acetate, and the aqueous layer was extracted twice with 1000 mL of a mixed solution of ethyl acetate/n-butanol (2/1). The extract was washed five times with 500 mL of water and was concentrated under reduced pressure. The obtained residue was solidified by treatment with ether, then dried. Thus 178.3 g of D-Ser(But)-Leu-Arg-Pro-NHEt (91.2% yield) was obtained.

Moreover, the melting point, optical rotation, Rf value of TLC and elementary analysis of the obtained compound were identical to those of D-Ser(But)-Leu-Arg-Pro-NHEt produced as described in Example 1 (1-3).

Example 3

Production of pGlu-His-Trp-Ser-Tyr-D-Leu-Leu-Arg-Pro-NHEt (SEQ ID NO:1)

(3-1) Production of Boc-D-Leu-Leu-Arg(Tos)-Pro-NHEt

Z-Leu-Arg(Tos)-Pro-NHEt 20.99 g produced as in Example 1 (1-2) was dissolved in 200 mL of methanol, then hydrogen was passed to the solution in the presence of 1.5 g of 10% palladium/carbon. The mixture was stirred at room temperature for 7 hours, the catalyst was removed, then the filtrate was concentrated under reduced pressure. The residue was solidified by treatment with ether. Thus, H-Leu-Arg(Tos)-Pro-NHEt was obtained.

H-Leu-Arg(Tos)-Pro-NHEt was dissolved in 80 mL of DMF and 200 mL of THF. With cooling the solution was neutralized with N-methylmorpholine. To the solution, a solution in which 8.86 g of Boc-D-Leu-OH and 23.02 g of HOSu were dissolved in 200 mL of THF, and 36.4 mL of WSC were added. Next the mixture was stirred at 0° C. for 5 minutes and at room temperature overnight. After confirmation with ninhidrin, the reaction mixture was concentrated under reduced pressure. To the residue, 500 mL of water was added, then the mixture was extracted 5 times with 200 mL of n-butanol and washed five times with water. The n-butanol layer was concentrated under reduced pressure, then the residue was solidified by treatment with ether. Thus 21.5 g of Boc-D-Leu-Leu-Arg(Tos)-Pro-NHEt (92.1% yield) was obtained.

The melting point, optical rotation, Rf of TLC and elementary analysis of Boc-D-Leu-Leu-Arg(Tos)-Pro-NHEt are shown below.

m.p.: 119–121° C.; $[\alpha]_D$: −45.2 (c=1.0, MeOH); Rf 0.50 (BuOH/AcOH/H$_2$O=4/1/5); Elementary analysis ($C_{30}H_{56}N_8O_6$); Calculated C, 57.67%; H, 9.03%; N, 17.93%; Found C, 57.43%; H, 8.89%; N, 17.80%.

(3-2) Production of Z-Ser-Tyr-D-Leu-Leu-Arg(Tos)-Pro-NHEt (SEQ ID NO:4)

Boc-D-Leu-Leu-Arg(Tos)-Pro-NHEt 25.8 g produced as described in the above (3-1) was dissolved in 10 mL of DCM. TFA 10 mL was added with ice cooling to the solution, then the mixture was stirred at room temperature for 30 minutes. Subsequently, the reaction mixture was concentrated under reduced pressure, 200 mL of ether was added to the residue so as to be solidified, then the product was dried. Thus H-D-Leu-Leu-Arg(Tos)-Pro-NHEt.TFA was obtained.

Z-Ser-Tyr-NHNH$_2$ 16.6 g was dissolved in 100 mL of DMF, and cooled to −20° C. with dry ice-ethanol. To the solution, 29.8 mL of 4N HCl-dioxane and 5.3 mL of isoamyl nitrite were added to obtain an azide compound. Next the mixture neutralized with 16.7 mL of triethylamine was transferred to 200 mL of DMF containing H-D-Leu-Leu-Arg(Tos)-Pro-NHEt.TFA. Then the mixture was stirred at −20° C. for 2 hours and at 4° C. for 17 hours, then it was concentrated. Water 500 mL was added to the residue, then the mixture was extracted 5 times with 200 mL of n-butanol and washed 5 times with water. The n-butanol layer was concentrated under reduced pressure, then the residue was solidified by treatment with ether. Thus, 25.0 g of Z-Ser-Tyr-D-Leu-Leu-Arg(Tos)-Pro-NHEt (83.2% yield) was obtained.

The melting point, optical rotation, Rf of TLC and elementary analysis of Z-Ser-Tyr-D-Leu-Leu-Arg(Tos)-Pro-NHEt are shown below.

m.p.: 114–118° C. (decomp.); $[\alpha]_D$: −30.1 (c=1.0, DMF); Rf: 0.32 (BuOH/AcOH/H$_2$O=4/1/5); Elementary analysis ($C_{45}H_{68}N_{10}O_{10}$); Calculated C, 59.45%; H, 7.54%; N, 15.41%; Found C, 59.33%; H, 7.52%; N, 15.32%.

(3-3) Production of H-Ser-Tyr-D-Leu-Leu-Arg-Pro-NHEt (SEQ ID NO:4)

Anisole 32 mL was added to 20.4 g of Z-Ser-Tyr-D-Leu-Leu-Arg(Tos)-Pro-NHEt produced as in the above (3-2), then the mixture was cooled to −70° C. with dry ice—ethanol. To the mixture, 200 mL of HF was added and stirred at 0° C. for 1 hour. Subsequently, the reaction mixture was concentrated under reduced pressure, the residue was treated with ether, and the deposited product was filtered and then vacuum-dried over sodium hydroxide. Thus 16.0 g of H-Ser-Tyr-D-Leu-Leu-Arg-Pro-NHEt (92.4% yield) was obtained.

The melting point, optical rotation, Rf of TLC and elementary analysis of H-Ser-Tyr-D-Leu-Leu-Arg-Pro-NHEt are shown below.

m.p.: 121–123° C.; $[\alpha]_D$: +11.0 (c=1.0, DMF); Rf: 0.20 (BuOH/AcOH/H$_2$O=4/1/5); Elementary analysis ($C_{37}H_{62}N_{10}O_8$); Calculated C, 57.35%; H, 8.06%; N, 18.07%; Found C, 57.21%; H, 8.01%; N, 18.10%.

(3-4) Production of pGlu-His-Trp-Ser-Tyr-D-Leu-Leu-Arg-Pro-NHEt (amino acids 1–9 of SEQ ID NO:1)

pGlu-His-Trp-Ser-Tyr-D-Leu-Leu-Arg-Pro-NHEt 1.33 g (76.4% yield) was obtained in the same manner as in Example 1 (1-11) except that 1.30 g of H-Ser-Tyr-D-Leu-Leu-Arg-Pro-NHEt produced as in the above (3-3) was used instead of H-Ser-Tyr-D-Ser(But)-Leu-Arg-Pro-NHEt.

The optical rotation, elementary analysis, and amino acid composition of pGlu-His-Trp-Ser-Tyr-D-Leu-Leu-Arg-Pro-NHEt are shown below.

$[\alpha]_D$: −32.0 (c=0.52, 5%AcOH); Elementary analysis ($C_{59}H_{84}N_{16}O_{12}$); Calculated C, 58.59%; H, 7.00%; N, 18.53%; Found C, 58.40%; H, 7.10%; N, 18.31%. Amino acid composition; Ser 1.05(1), Glu 1.08(1), Pro 0.99(1), Leu2.09(2), Tyr 0.92(1), His 0.93(1), Arg 1.06(1).

Example 4

Production of pglu-His-Trp-Ser-Try-D-Ser-(But)-Leu-Arg-Pro-Azgly-$NH_2$ (SEQ ID NO:1)

(4-1) Production of Z-Pro-Azgly-$NH_2$

Z-Pro-OH 24.9 g, 11.2 g of semicarbazide hydrochloride and 14.5 mL of triethylamine were dissolved in 200 mL of DMF. To the solution cooled to 0° C., 20.6 g of DCC was added and the mixture was stirred at 4° C. for 16 hours. Subsequently, dicyclohexylurea (DCU) was filtered off from the reaction mixture, and the filtrate was concentrated under reduced pressure. To the residue 500 mL of ethyl acetate was added, and the mixture was washed twice with 200 mL of water and concentrated under reduced pressure, then the residue was solidified by treatment with ether. Thus 16.7 g of Z-Pro-Azgly-$NH_2$ (54.3% yield) was obtained.

The melting point, optical rotation, Rf of TLC and elementary analysis of Z-Pro-Azgly-$NH_2$ are shown below.

m.p.: 189–190° C.; $[\alpha]_D$: −43.6 (c=1.4, DMF); Rf: 0.62 (BuOH/AcOH/$H_2O$=4/1/5); Elementary analysis ($C_{14}H_{18}N_4O_4$); Calculated C, 54.89%; H, 5.95%; N, 18.29%; Found C, 54.41%; H, 7.74%; N, 15.60%.

(4-2) Production of Boc-Arg($NO_2$)-Pro-Azgly-$NH_2$

Z-Pro-Azgly-$NH_2$ 16.5 g produced as described in the above (4-1) was dissolved in 500 mL of DMF, and hydrogen was passed to the solution in the presence of 1.1 g of 10% palladium/carbon. The mixture was stirred at room temperature for 7 hours, the catalyst was removed, then the filtrate was concentrated under reduced pressure. Ether 1500 mL was added to the residue to solidify the product, which then was dried. Thus, H-Pro-Azgly-$NH_2$.TFA was obtained.

Boc-Arg($NO_2$)-OH 13.5 g was dissolved in 100 mL of THF and cooled to −20° C. with dry ice—ethanol. To the solution, 3.3 mL of N-methylmorpholine and then 3.96 mL of isobutyl chloroformate were added dropwise, then the mixture was stirred at −20° C. for 1 minute, thereby producing a mixed acid anhydride. The obtained reaction mixture was mixed with 200 mL of a DMF solution (which was neutralized with N-methylmorpholine) containing H-Pro-Azgly-$NH_2$.TFA. Next the mixture was stirred at 0° C. for 5 minutes then at room temperature for 30 minutes, and concentrated under reduced pressure. Water 500 mL was added to the residue, and the mixture was extracted 5 times with 200 mL of n-butanol. Further the extract was washed 5 times with water, the n-butanol layer was concentrated under reduced pressure, then the residue was solidified by treatment with ether. Thus, 16.7 g of Boc-Arg($NO_2$)-Pro-Azgly-$NH_2$ (88.6% yield) was obtained.

The melting point, optical rotation, Rf of TLC and elementary analysis of Boc-Arg($NO_2$)-Pro-Azgly-$NH_2$ are shown below.

m.p. 135–137° C. (decomp.); $[\alpha]_D$: +35.3° (c=1.0, DMF); Rf: 0.49 (BuOH/AcOH/$H_2O$=4/1/5); Elementary analysis ($C_{17}H_{31}N_9O_7$); Calculated C, 43.12%; H, 6.60%; N, 26.62%; Found C, 54.41%; H, 7.74%; N, 15.60%.

(4-3) Production of Z-Leu-Arg($NO_2$)-Pro-Azgly-$NH_2$ (SEQ ID NO:2)

Boc-Arg($NO_2$)-Pro-Azgly-NHEt 110.54 g produced as described in the above (4-2) was dissolved in 150 mL of DCM. To the solution, 150 mL of TFA was added with ice cooling and the mixture was stirred at room temperature for 30 minutes. Next the reaction mixture was concentrated under reduced pressure, 1500 mL of ether was added to the residue to solidify the product, which was then dried. Thus H-Arg($NO_2$)-Pro-NHEt.TFA was obtained.

H-Arg($NO_2$)-Pro-NHEt.TFA was dissolved in a mixture of 80 mL of DMF and 200 mL of THF. With cooling the solution was neutralized with N-methylmorpholine. Subsequently to the solution, a solution wherein 53.06 g of Z-Leu-OH (0.2mole) and 23.02 g of HOSu (0.22mole) were dissolved in 200 mL of THF and 36.4 mL (0.2mole) of WSC were added, and the mixture was stirred at 0° C. for 5 minutes then at room temperature overnight. After confirmation with ninhydrin, the reaction mixture was concentrated under reduced pressure. Ethyl acetate 1500 mL was added to the residue, the mixture was washed twice with 500 mL of water and twice with 500 mL of saturated saline solution. After that, the ethyl acetate layer was concentrated under reduced pressure, the residue was solidified by treatment with ether, and the product was dried. Thus, 27.52 g of Z-Leu-Arg($NO_2$)-Pro-Azgly-$NH_2$ (SEQ ID NO:2) (98.6% yield) was obtained.

The melting point, optical rotation, Rf of TLC and elementary analysis of Z-Leu-Arg(NO)-Pro-Azgly-$NH_2$ are shown below.

m.p.: 88–90° C.; $[\alpha]_D$: −30.2 (c=1.5, DMF); Rf: 0.57 (BuOH/AcOH/$H_2O$=4/1/5); Elementary analysis ($C_{26}H_{40}N_{10}O_8$); Calculated C, 50.31%; H, 6.50%; N, 22.57%; Found C, 50.24%; H, 6.41%; N, 22.45%.

(4-4) Production of Z-D-Ser(But)-Leu-Arg-Pro-Azgly-$NH_2$ (amino acids 3–6 of SEQ ID NO:4)

Z-Leu-Arg($NO_2$)-Pro-Azgly-$NH_2$ (SEQ ID NO:2) produced in the above (4-3) 16.5 g was dissolved in 500 mL of DMF, and hydrogen was passed to the solution in the presence of 1.1 g of 10% palladium/carbon. The mixture was stirred at room temperature for 7 hours, the catalyst was removed and then the filtrate was concentrated under reduced pressure. Ether 1500 mL was added to the residue to solidify and the product was dried. Thus H-Leu-Arg-Pro-Azgly-$NH_2$ (SEQ ID NO:3) was obtained.

Z-D-Ser(But)-OH 8.86 g was dissolved in 100 mL of THF, then the solution was cooled to −20° C. with dry ice—ethanol. To the solution, 3.3 mL of N-methylmorpholine and then 3.96 mL of isobutyl chloroformate were added dropwise. The mixture was stirred at −20° C. for 1 minute, thereby producing a mixed acid anhydride. The obtained reaction mixture was mixed with 200 mL of DMF solution containing H-Leu-Arg-Pro-Azgly-$NH_2$ (neutralized with N-methylmorpholine), the mixture was stirred at 0° C. for 5 minutes and then at room temperature for 30 minutes, finally the reaction mixture was concentrated under reduced pressure. Water 500 mL was added to the residue, then the mixture was extracted 5 times with 200 mL of n-butanol. After the extract was washed 5 times with water, the n-butanol layer was concentrated under reduced pressure, then the residue was solidified by treatment with ether. Thus 16.9 g of Z-D-Ser(But)-Leu-Arg-Pro-Azgly-$NH_2$ (78.3% yield) was obtained.

The melting point, optical rotation, Rf of TLC and elementary analysis of Z-D-Ser(But)-Leu-Arg-Pro-Azgly-$NH_2$ are shown below.

m.p.: 115–118° C.; $[\alpha]_D$: −45.8 (c=1.0, DMF); Rf: 0.51 (BuOH/AcOH/$H_2O$=4/1/5); Elementary analysis ($C_{33}H_{54}N_{10}O_8$); Calculated C, 55.14%; H, 7.57%; N, 19.48%; Found C, 55.01%; H, 7.42%; N, 19.33%.

(4-5) Production of Z-Ser-Tyr-D-Ser(But)-Leu-Arg-Pro-Azgly-NH$_2$ (SEQ ID NO:4)

Z-D-Ser(But)-Leu-Arg-Pro-Azgly-NH$_2$ 26.7 g produced as described in the above (4-4) was dissolved in 500 mL of methanol, and hydrogen was passed to the solution in the presence of 1.9 g of 10% palladium/carbon. The mixture was stirred at room temperature for 7 hours, the catalyst was removed, then the filtrate was concentrated under reduced pressure. The residue was treated with ether, the deposited product was filtered, then the product was vacuum -dried over sodium hydroxide. Thus H-D-Ser(But)-Leu-Arg-Pro-Azgly-NH$_2$ was obtained.

Z-Ser-Tyr-NHNH$_2$ 18.5 g produced as in Example 1 (1-5) was dissolved in 150 mL of DMF, and the solution was cooled to −20° C. with dry ice—ethanol. 4N HCl-dioxane 33.4 mL and 6.0 mL of isoamyl nitrite were added to the solution so as to obtain an azide compound. Further 18.7 mL of triethylamine was added to neutralize the mixture. The mixture was transferred to 150 mL of a DMF solution containing H-D-Ser(But)-Leu-Arg-Pro-Azgly-NH$_2$. After the mixture was stirred at −20° C. for 2 hours then at 4° C. for 17 hours, it was concentrated. Water 500 mL was added to the residue, and the product was extracted 5 times with 200 mL of n-butanol. Next the extract was washed 5 times with water, the n-butanol layer was concentrated under reduced pressure, finally the residue was solidified by treatment with ether. Thus 28.3 g of Z-Ser-Tyr-D-Ser(But)-Leu-Arg-Pro-Azgly-NH$_2$ (78.6% yield) was obtained.

The melting point, optical rotation, Rf of TLC and elementary analysis of Z-Ser-Tyr-D-Ser(But)-Leu-Arg-Pro-Azgly-NH$_2$ are shown below.

m.p. 110–113° C. (decomp.); $[\alpha]_D$: −28.2 (c=1.0, DMF); Rf: 0.36 (BuOH/AcOH/H$_2$O=4/1/5); Elementary analysis (C$_{45}$H$_{68}$N$_{12}$O$_{12}$); Calculated C, 55.77%; H, 7.07%; N, 17.34%; Found C, 55.64%; H, 7.01%; N, 17.29%.

(4-6) Production of H-Ser-Tyr-D-Ser(But)-Leu-Arg-Pro-Azgly-NH$_2$

Z-Ser-Tyr-D-Ser(But)-Leu-Arg-Pro-Azgly-NH$_2$ 25.4 g produced as described in the above (4-5) was dissolved in 500 mL of methanol, and hydrogen was passed to the solution in the presence of 1.3 g of 10% palladium/carbon. After the mixture was stirred at room temperature for 7 hours, the catalyst was removed and then the filtrate was concentrated under reduced pressure.

The residue was solidified by treatment with ether. Thus 20.7 g of H-Ser-Tyr-D-Ser(But)-Leu-Arg-Pro-Azgly-NH$_2$ (94.6% yield) was obtained.

The melting point, optical rotation, Rf of TLC and elementary analysis of H-Ser-Tyr-D-Ser(But)-Leu-Arg-Pro-Azgly-NH$_2$ are shown below.

m.p.: 120–122° C.; $[\alpha]_D$: +11.2 (c=1.0, DMF); Rf: 0.31 (BuOH/AcOH/H$_2$O=4/1/5); Elementary analysis (C$_{37}$H$_{62}$N$_{12}$O$_{10}$); Calculated C, 53.22%; H, 7.48%; N, 20.13%; Found C, 53.19%; H, 7.43%; N, 20.01%.

(4-7) Production of pGlu-His-Trp-Ser-Tyr-D-Ser(But)-Leu-Arg-Pro-Azgly-NH$_2$ pGlu-His-Trp-Ser-Tyr-D-Ser(But)-Leu-Arg-Pro-Azgly-NH$_2$ 1.29 g (75.9% yield) was obtained by the same manner as in Example 1 (1-11) except that 1.30 g of H-Ser-Tr-D-Ser(But)-Leu-Arg-Pro-Azgly-NH$_2$ produced in the above (4-6) was used instead of H-Ser-Tyr-D-Ser(But)-Leu-Arg-Pro-NHEt.

The optical rotation, elementary analysis and amino acid composition of pGlu-His-Trp-Ser-Tyr-D-Ser(But)-Leu-Arg-Pro-Azgly-NH$_2$ are shown below.

$[\alpha]_D$: −52.4 (c=1.0, DMF); Elementary analysis (C$_{59}$H$_{84}$N$_{18}$O$_{14}$); Calculated C, 55.82%; H, 6.67%; N, 19.86%; Found C, 55.70%; H, 6.55%; N, 19.72%.

Amino acid composition; Ser 2.02(2), Glu 1.07(1), Pro 1.00(1), Leu 1.03(1), Tyr 0.92(1), His 0.94(1), Arg 1.02(1).

Example 5

Production of pGlu-His-Trp-Ser-Tyr-D-Trp-Leu-Arg-Pro-Gly-NH$_2$-(SEQ ID NO:1)

(5-1) Production of H-Ser-Tyr-D-Trp-Leu-Arg-Pro-Gly-NH$_2$

Solid phase synthesis is performed by using Peptide Synthesizer 9600 manufactured by Milligen Bioresearch Corporation.

First 694 mg of p-methylbenzhydrylamine(MBHA) resin (manufactured by PEPTIDE INSTITUTE, INC., amino group 0.72 mmol/g) was put into a reaction vessel for peptide solid phase synthesis, and treated with stirring in turn with 8 mL of DCM (4 times, 1 minute each), 8 mL of DCM solution containing 60% TFA (20 minutes), 4 mL of DCM (3 times, 15 seconds each), 3 mL of DMF solution containing 1 mL of DIEA (twice, 1 minute each), and 8 mL of DMF (6 times, 40 seconds each) under argon stream. Further filtration was performed at each treatment.

On the other hand, 2 mmole of Boc-Gly-OH corresponding to the tenth amino acid residue of the amino acid sequence of pGlu-His-Trp-Ser-Tyr-D-Trp-Leu-Arg-Pro-Gly-NH$_2$ was dissolved in 4 mL of DCM. The solution was put into an amino acid activation container, 3 mL of DCC (0.5M-DCM solution) and 4 mL of HOBt (0.5M-DCM solution) were added to the solution, then the mixture was allowed to react for 30 minutes. The reaction mixture was filtered and transferred to a concentration container. Then 3 mL of DMF was added to the mixture, and the DCM was distilled off under argon stream. Next the residue to which 3 mL of DMF was added was transferred to the said reaction vessel for peptide solid phase synthesis, then allowed to react for 30 minutes. Subsequently the product was washed with 8 mL of DCM (6 times, 20 seconds each). Further 2 mmol of Boc-Gly-OH was dissolved in 4 mL of DCM, the so-called double-coupling method was performed wherein the similar operation was repeated in an amino acid activation container, then the product was filtered, thereby obtaining Boc-Gly-MBHA resin.

Subsequently, the obtained Boc-Gly-MBHA resin was washed with 8 mL of DCM (4 times, 1 minute each) and then it was filtered. After that the product was treated with stirring in turn with 8 mL of DCM solution containing 60% TFA (20 minutes), 4 mL of DCM (3 times, 15 seconds each), 3 mL of DMF solution containing 1 mL of DIEA (twice, 1 minute each), and 8 mL of DMF (6 times, 40 seconds each) under argon stream. In addition, filtration was performed at each treatment. Next, 2 mmole of Boc-Pro-OH corresponding to the ninth amino acid residue of the amino acid sequence of pGlu-His-Trp-Ser-Tyr-D-Trp-Leu-Arg-Pro-Gly-dissolved in 4 mL of DCM. DCC (0.5M-DCM solution) 1.5 mL was added to the solution in an amino acid activation container, then the solution was allowed to react for 7 minutes. After that, the reaction mixture was filtered and transferred to a concentration container. Then 3 mL of DMF was added to the reaction mixture, and the DCM was distilled off under argon stream. Next the residue to which 3 mL of DMF was added was transferred to said reaction vessel for peptide solid phase synthesis, then allowed to react for 30 minutes. Subsequently the product was washed with 8 mL of DCM (6 times, 20 seconds each), then filtered, thereby obtaining Boc-Pro-Gly-MBHA resin.

Eight to fourth amino acids are coupled in order by means of amino group protected amino acids as shown in Table 2 below.

TABLE 2

| Amino acid order | Protected amino acid | Amount used (mmol) |
|---|---|---|
| 8 | Boc-Arg(Tos)-OH | 2 × 2 |
| 7 | Boc-Leu-OH | 2 |
| 6 | Boc-D-Trp-OH | 2 |
| 5 | Boc-Tyr(Bzl)-OH | 2 |
| 4 | Boc-Ser(Bzl)-OH | 2 |

In above solid phase synthesis, the double coupling was performed when Arg used. Thus 2.76 g of protected peptide-MBHA resin, Boc-Ser(Bzl)-D-Trp-Leu-Arg(Tos)-Pro-Gly-MBHA resin was obtained.

To the above 2.76 g of protected peptide-MBHA resin, 5 mL of anisole and then 25 mL of hydrogen fluoride anhydride were added, then the product was stirred at 0° C. for 1 hour. After the reaction, hydrogen fluoride anhydride was distilled off under reduced pressure, then the residue was washed with ether. Thus 1.30 g of H-Ser-Tyr-D-Trp-Leu-Arg-Pro-Gly-NH$_2$ was obtained.

The optical rotation, Rf of TLC, and elementary analysis of H-Ser-Tyr-D-Trp-Leu-Arg-Pro-Gly-NH$_2$ are shown below.

$[\alpha]_D$: −50.4 (c=1.0, MeOH); Rf: 0.13 (BuOH/AcOH/H$_2$O=4/1/5); Elementary analysis (C$_{59}$H$_{84}$N$_{16}$O$_{12}$·AcOH·2H$_2$O); Calculated C, 54.31%; H, 7.04%; N, 17.27%; Found C, 54.20%; H, 6.89%; N, 16.97%.

(5-2) Production of pGlu-His-Trp-Ser-Tyr-D-Trp-Leu-Arg-Pro-Gly-NH$_2$ (SEQ ID NO:1)

pGlu-His-Trp-Ser-Tyr-D-Trp-Leu-Arg-Pro-Gly-NH$_2$ 1.26 g (75.45% yield) was obtained by the same manner as in Example 1 (1-11) except that 1.30 g of H-Ser-Tyr-D-Trp-Leu-Arg-Pro-Gly-NH$_2$ produced in the above (5-1) was used instead of H-Ser-Tyr-D-Ser(But)-Leu-Arg-Pro-Gly-NHEt.

The optical rotation, elementary analysis and amino acid composition of pGlu-His-Trp-Ser-Tr-D-Trp-Leu-Arg-Pro-Gly-NH$_2$ are shown below.

$[\alpha]_D$: −56.6 (c=1.0, H$_2$O); Elementary analysis (C$_{64}$H$_{82}$N$_{18}$O$_{13}$·AcOH·2H$_2$O); Calculated C, 56.32%; H, 6.44%; N, 17.91%; Found C, 56.20%; H, 6.38%; N, 16.97%. Amino acid composition; Ser 0.98(1), Glu 1.07(1), Gly 1.01(1), Pro 0.99(1), Leu 1.00(1), Tyr 0.92(1), His 0.95(1), Arg 1.08(1)

Example 6

Production of Glu-His-Trp-Ser-Tyr-(2-naphthyl)-D-Ala-Leu-Arg-Pro-Gly-NH$_2$ (SEQ ID NO:1)

(6-1) Production of H-Ser-Tyr-(2-naphthyl)-D-Ala-Leu-Arg-Pro-Gly-NH$_2$ (amino acids 4–10 of SEQ ID NO:1)

H-Ser-Tyr-(2-naphthyl)-D-Ala-Leu-Arg-Pro-Gly-NH$_2$ 0.98 g was obtained by the same treatment as in Example 5 (5-1) except that Boc-D-(2-naphthyl)-D-Ala-OH was used instead of Boc-D-Trp-OH corresponding to the 6$^{th}$ amino acid residue.

The optical rotation, Rf of TLC, and elementary analysis of H-Ser-Tyr-(2-naphthyl)-D-Ala-Leu-Arg-Pro-Gly-NH$_2$ are shown below.

$[\alpha]_D$: −44.1 (c=1.0, MeOH); Rf: 0.15; Elementary analysis (C$_{47}$H$_{66}$N$_{12}$O$_{10}$); Calculated C, 58.86%; H, 6.94%; N, 17.52%; Found C, 58.72%; H, 6.88%; N, 17.49%.

(6-2) Production of pGlu-His-Trp-Ser-Tyr-(2-naphtyl)-D-Ala-Leu-Arg-Pro-Gly-NH$_2$ (SEQ ID NO:1)

pGlu-His-Trp-Ser-Tyr-(2-naphthyl)-D-Ala-Leu-Arg-Pro-Gly-NH$_2$ 0.93 g (76.2% yield) was obtained by the same manner as in Example 1 (1-11) except that 0.98 g of H-Ser-Tyr-(2-naphthyl)-D-Ala-Leu-Arg-Pro-Gly-NH$_2$ produced in the above (6-1) was used instead of H-Ser-Tyr-D-Ser(But)-Leu-Arg-Pro-NHEt.

The optical rotation, elementary analysis and amino acid composition of pGlu-His-Trp-Ser-Tyr-(2-naphthyl)-D-Ala-Leu-Arg-Pro-Gly-NH$_2$ are shown below.

$[\alpha]_D$: −50.3 (c=1.0, H$_2$O); Elementary analysis (C$_{69}$H$_{88}$N$_{18}$O$_{14}$); Calculated C, 59.47%; H, 6.37%; N, 18.09% Found C, 59.40%; H, 6.33%; N, 17.98%. Amino acid composition; Ser 0.98(1), Glu 1.05(1), Gly 1.00(1), Pro 1.03(1), Leu 1.00(1), Tyr 0.93(1), His 0.94(1), Arg 1.07(1)

Example 7

Production of pGlu-His-Trp-Ser-Tyr-Gly-Leu-Arg-Pro-Gly-NH$_2$ (SEQ ID NO:1)

(7-1) Production of H-Ser-Tyr-Gly-Leu-Arg-Pro-Gly-NH$_2$ (SEQ ID NO:4)

H-Ser-Tyr-Gly-Leu-Arg-Pro-Gly-NH$_2$ (SEQ ID NO:4) 1.12 g was obtained by the same treatment as in Example 5 (5-1) except that Boc-Gly-OH was used instead of Boc-D-Trp-OH corresponding to the 6$^{th}$ amino acid residue.

The optical rotation, Rf of TLC, and elementary analysis of H-Ser-Tyr-Gly-Leu-Arg-Pro-Gly-NH$_2$ are shown below.

$[\alpha]_D$: −40.1 (c=1.0, MeOH); Rf: 0.10 (BuOH/AcOH/H$_2$O=4/1/5); Elementary analysis (C$_{33}$H$_{53}$N$_{11}$O$_9$); Calculated C, 53.00%; H, 7.14%; N, 20.60%; Found C, 53.20%; H, 6.89%; N, 20.97%.

(7-2) Production of pGlu-His-Trp-Ser-Tyr-Gly-Leu-Arg-Pro-Gly-NH$_2$ (SEQ ID NO:1)

pGlu-His-Trp-Ser-Tyr-Gly-Leu-Arg-Pro-Gly-NH$_2$ (SEQ ID NO:1) 1.16 g (76.3% yield) was obtained by the same method as in Example 1 (1-11) except that 1.12 g of H-Ser-Tyr-Gly-Leu-Arg-Pro-Gly-NH$_2$ (SEQ ID NO:4) produced in the above (6-1) was used instead of H-Ser-Tyr-D-Ser(But)-Leu-Arg-Pro-NHEt.

The elementary analysis and amino acid composition of pGlu-His-Trp-Ser-Tyr-Gly-Leu-Arg-Pro-Gly-NH$_2$ are shown below.

Elementary analysis (C$_{55}$H$_{75}$N$_{17}$O$_{13}$·AcOH·2H$_2$O); Calculated C, 53.55%; H, 6.54%; N, 18.63%; Found C, 53.85%; H, 6.89%; N, 18.97%. Amino acid composition; Ser 1.01(1), Glu 1.03(1), Gly 2.01(2), Pro 0.98(1), Leu 1.01(1), Tyr 0.94(1), His 0.94(1), Arg 1.08(1).

Industrial Applicability

The method according to the present invention facilitates separation and purification of LH-RH derivatives without side reaction such as racemization, because of the use of an enzyme reaction. Moreover the method according to the invention is extremely useful in industrial use because it leads to high yields and allows recovery and recycling of unreacted peptide fragments.

What is claimed is:

1. A method of producing a LH-RH derivative represented by formula (1):

pGlu-His-Trp-Ser-Tyr-X-Leu-Arg-Pro-Y (SEQ ID NO:1)   (1)

wherein

X denotes an amino acid selected from the group consisting of D-Leu, D-Ser(But), D-Trp, (2-napthyl)-D-Ala, and Gly;

Y denotes Gly-NH$_2$, Azgly(Azaglycine)-NH$_2$ or NHR$^2$; and

R$^2$ is a lower alkyl, comprising reacting a peptide fragment represented by formula (2):

pGlu-His-Trp-OR$^1$   (2)

wherein

R$^1$ denotes a lower alkyl, with a peptide fragment shown represented by formula (3):

H-Ser-Tyr-X-Leu-Arg-Pro-Y (SEQ ID NO:4)   (3)

wherein

X and Y are as described above, catalyzed by chymotrypsin in a reaction medium comprising 1-butanol.

2. The method according to claim 1, wherein the reaction medium further comprises water.

3. The method according to claim 1 wherein the reaction medium is water saturated with 1-butanol.

4. The method according to claim 3, wherein the reaction medium further comprises a buffer.

5. The method according to claim 4, wherein the buffer is selected from the group consisting Tris-hydrochloric acid, MacIlvaine's buffer, phosphate buffer, ammonium acetate buffer, Atkins & Pantin buffer, and Veronal buffer.

6. The method according to claim 1, wherein R$^1$ is an alkyl group having 1 to 3 carbons.

7. The method according to claim 1, wherein R$^2$ is an alkyl group having 1 to 3 carbons.

8. The method according to claim 1, wherein the chymotrypsin is immobilized.

9. The method according to claim 1, which is conducted at a pH from 5.0 to 10.0.

10. The method according to claim 1, which is conducted at a pH from 7.5 to 8.5.

11. The method according to claim 1, wherein the reaction medium does not contain saturated potassium chloride.

12. The method according to claim 11, which is conducted at a temperature is from 0 to 50° C.

13. The method according to claim 11, which is conducted at a temperature is from 0 to 20° C.

* * * * *

SEQUENCE LISTING

<160> NUMBER OF SEQ ID NOS: 4

<210> SEQ ID NO 1
<211> LENGTH: 10
<212> TYPE: PRT
<213> ORGANISM: Artificial Sequence
<220> FEATURE:
<221> NAME/KEY: misc_feature
<223> OTHER INFORMATION: Description of Artificial Sequence: synthetic
      peptide
<221> NAME/KEY: misc_feature
<222> LOCATION: (1)..(1)
<223> OTHER INFORMATION: pyroglutamic acid
<221> NAME/KEY: misc_feature
<222> LOCATION: (6)..(6)
<223> OTHER INFORMATION: Xaa may be D-Leu, D-Trp, D-Ala, D-Phe, D-Val,
      D-His, D-Ser(But), (2-napthyl)-D-Ala, and Glycine
<221> NAME/KEY: misc_feature
<222> LOCATION: (10)..(10)
<223> OTHER INFORMATION: Xaa may be Glycine, Gly-NH2, Azgly-NH2 or NHR2
      (where R2 is a lower alkyl)

<400> SEQUENCE: 1

Xaa His Thr Ser Tyr Xaa Leu Arg Pro Xaa
1               5                   10

<210> SEQ ID NO 2
<211> LENGTH: 4
<212> TYPE: PRT
<213> ORGANISM: Artificial Sequence
<220> FEATURE:
<221> NAME/KEY: misc_feature
<223> OTHER INFORMATION: Description of Artificial Sequence: synthetic
      peptide
<221> NAME/KEY: misc_feature
<222> LOCATION: (2)..(2)
<223> OTHER INFORMATION: Xaa is Arg(NO2)
<221> NAME/KEY: misc_feature
<222> LOCATION: (4)..(4)
<223> OTHER INFORMATION: Xaa is Azgly-NH2

<400> SEQUENCE: 2

Leu Xaa Pro Xaa
1

<210> SEQ ID NO 3
<211> LENGTH: 4
<212> TYPE: PRT
<213> ORGANISM: Artificial Sequence
<220> FEATURE:
<221> NAME/KEY: misc_feature
<223> OTHER INFORMATION: Description of Artificial Sequence: synthetic
      peptide
<221> NAME/KEY: misc_feature
<222> LOCATION: (4)..(4)
<223> OTHER INFORMATION: Xaa is Azgly-NH2

<400> SEQUENCE: 3

Leu Arg Pro Xaa
1

<210> SEQ ID NO 4
<211> LENGTH: 7
<212> TYPE: PRT
<213> ORGANISM: Artificial Sequence
<220> FEATURE:
<221> NAME/KEY: misc_feature
<223> OTHER INFORMATION: Description of Artificial Sequence: synthetic
      peptide
<221> NAME/KEY: misc_feature -continued

```
<222> LOCATION: (3)..(3)
<223> OTHER INFORMATION: Xaa is D-Leu, D-Ser(But), D-Trp,
      (2-napthyl)-D-Ala, or Gly
<221> NAME/KEY: misc_feature
<222> LOCATION: (7)..(7)
<223> OTHER INFORMATION: Xaa is Gly-NH2, Azgly-NH2 or NHR2 (where R2
      is lower alkyl)

<400> SEQUENCE: 4

Ser Tyr Xaa Leu Arg Pro Xaa
1               5
```